United States Patent [19]

Huibers et al.

[11] 4,433,184
[45] Feb. 21, 1984

[54] MULTI-STAGE CATALYTIC CONVERSION OF ALDOSES TO ALDITOLS

[75] Inventors: Derk T. A. Huibers, Pennington, N.J.; James C. Chao, West Nyack, N.Y.; Rajni C. Shah, Lawrenceville, N.J.

[73] Assignee: HRI, Inc., Gibbsboro, N.J.

[21] Appl. No.: 258,225

[22] Filed: Apr. 27, 1981

[51] Int. Cl.³ .............................................. C07H 1/00
[52] U.S. Cl. .................................................... 568/863
[58] Field of Search ......................................... 568/863

[56] References Cited

U.S. PATENT DOCUMENTS

| | | | |
|---|---|---|---|
| 2,650,941 | 9/1953 | Koome et al. | 568/863 |
| 3,329,729 | 7/1967 | Brundner et al. | 568/863 |
| 4,258,222 | 3/1981 | Mohring | 568/863 |
| 4,322,569 | 3/1982 | Chao et al. | 568/863 |

Primary Examiner—Robert Gerstl
Attorney, Agent, or Firm—V. A. Mallare; F. A. Wilson

[57] ABSTRACT

Monosaccharides, such as glucose-water solution, are catalytically hydrogenated by being passed through multiple reaction zones connected in series and each containing a high-activity supported nickel catalyst to produce 99.8 W % overall conversion to an alditol solution such as sorbitol. The pH of liquid in each reaction zone is controlled to between 4.5 and 7 by adding an alkali solution such as sodium hydroxide to the feed to prevent acid leaching of catalyst metal and to help maintain catalyst activity therein. Reaction zone conditions used are 130°–180° C. temperature, 500–2000 psig hydrogen partial pressure, and a ratio of hydrogen gas/feed liquid within the range of about 500–5000. Feedstream liquid space velocity is maintained within range of 0.5–16 $V_f/Hr/V_c$, with higher space velocities being used for achieving lower incremental conversion desired in the subsequent reaction zones to help maintain pH of the effluent liquid within the desired range. The first reactor is preferably a back-mixed ebullated-catalyst-bed type to achieve 60–80 W % incremental conversion, the last reactor is a fixed-catalyst-bed type to achieve 5–20 W % incremental conversion, and three catalytic reaction zones are preferred.

18 Claims, 4 Drawing Figures

REACTION CONVERSION INDEX Vs. INVERSE SPACE VELOCITY
FOR MULTI-STAGE AND SINGLE STAGE REACTION ically high. To overcome these batch process handicaps, a continuous hydrogenation process using a suspended Raney nickel catalyst powder and two stirred tank reactors in series was developed and is used by some companies, as described by Haideggar et al in *Industrial & Engineering Chemistry* Vol. 7, No. 1, January 1968, pp. 107–110. However, a remaining disadvantage is the need to filter the catalyst from the product liquid in order to recycle the catalyst, and doing this without reducing the activity of the recycled catalyst by its exposure to air (oxygen).

MULTI-STAGE CATALYTIC CONVERSION OF ALDOSES TO ALDITOLS

BACKGROUND OF INVENTION

1. Field of Invention

This invention pertains to the multi-stage catalytic hydrogenation conversion of monosaccharides, such as glucose, to produce alditol products, such as high-purity sorbitol. It pertains more particularly to a continuous process for catalytic hydrogenation of such monosaccharides using a bace-mixed type reaction zone as first stage and at least one fixed-catalyst-bed type reactor connected in series, and all operated to control pH of the reaction zone liquid and maintain catalyst activity while producing a high-purity sorbitol product.

2. Description of Prior Art

Sorbitol can be produced commercially from glucose through either electrolytic reduction, enzymatic, or catalytic hydrogenation processes, but for economic reasons the catalytic hydrogenation processes for making sorbitol have largely replaced the other two processes. A batch autoclave reaction process using a Raney nickel powder catalyst is presently the major glucose hydrogenation process used in industry. However, batch processes have the disadvantage that new catalyst must be made in situ for each batch of feed. Although such catalyst can be filtered and reused, about 25% is lost and must be replaced with new catalyst. Another disadvantage of batch process plants is that their annual capacity relative to reaction volume is very small, which requires large, expensive reactors. Also, their requirements of steam, power and labor are relatively high. To overcome these batch process handicaps, a continuous hydrogenation process using a suspended Raney nickel catalyst powder and two stirred tank reactors in series was developed and is used by some companies, as described by Haideggar et al in *Industrial & Engineering Chemistry* Vol. 7, No. 1, January 1968, pp. 107–110. However, a remaining disadvantage is the need to filter the catalyst from the product liquid in order to recycle the catalyst, and doing this without reducing the activity of the recycled catalyst by its exposure to air (oxygen).

It has been further reported by the Haidegger article that VEB Deutsches Hydrierwork uses a continuous catalytic fixed-bed process for converting glucose to sorbitol, using a supported mixed copper/nickel catalyst. However, this process requires a relatively high hydrogen pressure of almost 3000 psig, and low liquid hourly space velocity. It was further reported by Haidegger that local overheating of the catalyst surface due to the heat of the hydrogenation reaction led to isomerization, cracking, and carmel formation, so that the product sorbitol contained a significant amount of mannitol. Thus, flow conditions in such fixed-catalyst-bed processes were regarded as less desirable than in continuous reactors using suspended catalysts.

Other processes for the batch-type catalytic hydrogenation of sugars to produce sorbitol and similar products are described in U.S. Pat. Nos. 1,963,999 and 1,990,245. U.S. Pat. No. 2,650,941 to Koome discloses a continuous process for catalytic conversion of carbohydrates in aqueous solutions to produce polyhydric alcohols, using one or more fixed-bed reactors connected in series. Useful reaction conditions are within the range of 100°–165° C. and 45–200 atmospheres hydrogen pressure. However, liquid space velocities were low, being only about 0.15 liter of 40% glucose per liter of catalyst in both reactors to achieve a maximum glucose conversion of 98.8%, while catalyst life was not disclosed.

U.S. Pat. No. 3,329,729 to Brandner discloses a multi-stage batch-type catalytic hydrogenation process for converting a mixture of glucose and fructose to produce mannitol and sorbitol. The feed contains 20–80% by weight sugars, and the catalyst contains about 20% nickel. Useful reaction conditions are in the range of 50°–80° C. temperature and hydrogen pressure of 500–3000 psig. U.S. Pat. No. 3,538,019 to Capik discloses a catalyst composed of nickel and nickel phosphate on an inert carrier, having total nickel of 12–45 W %. Such catalysts are useful for producing polyhydric alcohols from carbohydrates, and are used as suspensions with the carbohydrate feed. Useful reaction conditions are 120°–210° C. temperature and 25–200 atmospheres pressure.

There remains a commercial need for an economical continuous process to produce high-purity, USP-grade sorbitol solution from glucose, which specifies a maximum content of reducing sugars, including glucose of only 0.21 W %. An earlier process developed by applicants used a continuous fixed-bed single-stage catalytic hydrogenation process for converting glucose to sorbitol. By using a preferred high nickel-containing catalyst and under preferred operating conditions, 90 to 99% of glucose in the feed can be converted to sorbitol, and the catalyst activity can be maintained for up to about 100 hours before regeneration is required. However, the catalyst life for this process needs to be increased appreciably to reduce the cost of catalyst regeneration or replacement. Also, because a USP-grade sorbitol solution must contain only a minimal amount of reducing sugars, this requires at least 99 W % conversion of a feedstock containing 40 W % glucose to sorbitol product. It was unexpectedly observed that acidity develops in the reaction solution and is a major cause for deactivation of the catalyst. Gluconic acid is generated in the process as a side product and leaches nickel metal from the catalyst, thus causing deactivation of the catalyst and contamination of the product with nickel. Such deactivation does not occur with a ruthenium catalyst as described in U.S. Pat. No. 2,868,847 to Boyers; however, the ruthenium catalyst tested had a much lower activity than nickel catalyst.

In order to achieve the goals of producing USP-grade sorbitol solution and also substantially extending catalyst useful life, an improved multi-stage process sequence was conceived and successfully tested. Results showed the effectiveness of this new process for achieving the requirements of producing a USP-grade sorbitol solution product and maintaining long life for the catalyst.

SUMMARY OF INVENTION

The present invention provides an improved continuous, multi-stage process for catalytic hydrogenation and conversion of aldoses and monosaccharides such as glucose to produce alditols such as high-purity sorbitol, and utilizes at least two catalytic reaction stages or zones connected in series flow arrangement. The pH of the effluent liquid from each reaction zone is maintained above about 4.5, and preferably within the range of 5–7, by a combination of adding an alkali solution to the feedstream to each zone to control the feedstream pH to a range of about 7–13, and also limiting the aldose conversion percentage increment achieved in each zone to a specific range. This arrangement substantially prevents the undesirable formation of acids such as gluconic acid in each reaction zone, and thus prevents the acid leaching of active metals from the catalyst and thereby maintains high catalyst activity and long useful life.

The first reaction zone for this process preferably uses a back-mixed-type reactor, which provides for mixing a portion of reactor liquid with the feedstream, and thereby helps control the pH of the reaction zone liquid within the desired range and prevents deactivation of the catalyst. The last reaction zone in series is a fixed-bed type catalytic reactor, which is essential in achieving high conversions in an economic fashion. The process operating parameters should usually be selected so that the incremental percentage catalytic conversion of monosaccharides achieved in a first-stage back-mixed-type reactor is within the range of about 20–80 W %, and the incremental percentage conversion achieved in each subsequent fixed-bed-type reactor is about 5–20 W % in order to maintain high reaction rate constants by maintaining the desired pH of the reactor liquid, and thus extend the useful life of the catalyst. Furthermore, the product liquid composition increment achieved in each fixed-bed reaction stage or zone should not exceed about 35 W %, and preferably should not exceed about 20 W %. The total number of reaction stages or reactors used in this process will depend on the type of reactor and the operating conditions used, and can be optimized considering the cost of the reactors and the cost of catalyst used, and up to ten reactors connected to series could be used if desired.

DESCRIPTION OF THE INVENTION

Figure 1:
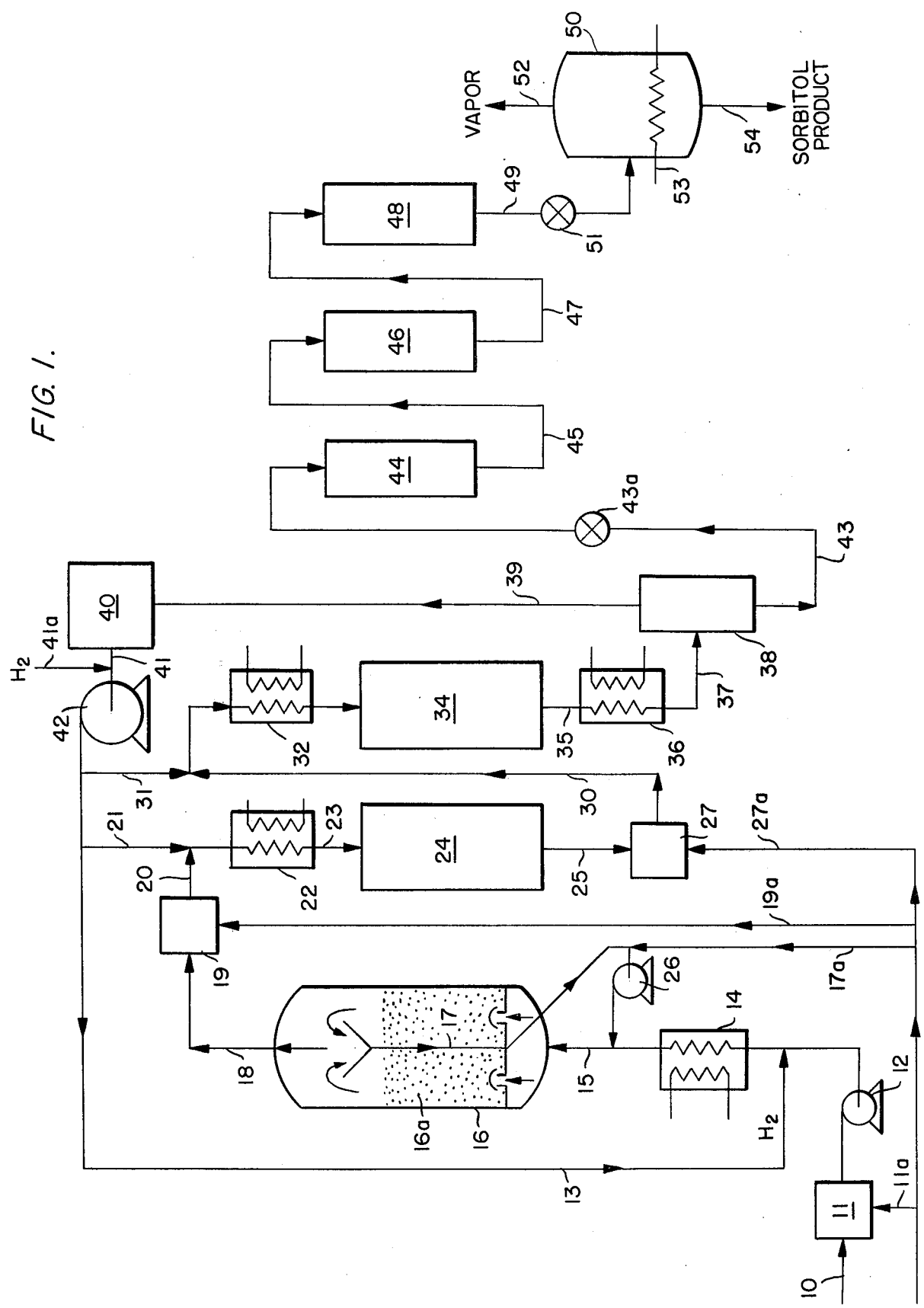
FIG. 1 is a schematic flow diagram of a three-stage, catalytic process for conversion of monosaccharides to produce sorbitol solution, followed by product purification steps.

The broad hydrogenation reaction conditions used in this improved multi-stage, catalytic hydrogenation process for achieving high conversion of monosaccharides to product high-purity sorbitol produce are within the range of 130°–180° C. (266°–356° F.) temperature, 500–2000 psig hydrogen partial pressure, and feed rate or liquid space velocity of 0.5–16 $V_f/Hr/V_c$ (volume feed solution per hour per total volume of catalyst in all reactors) to achieve up to 99.9 W % overall conversion, or even higher if lower incremental conversion per reaction stage is used. Alternatively, the space velocity based on weight of monosaccharide in the feedstream should be within the range of about 0.30–10 gm/hr/cc catalyst, and preferably is 0.40–8 gm/hr/cc. The aldose concentration in the feedstream will usually range between about 10 and 60 W %. To maintain catalyst activity and long life, it is necessary to maintain pH of the liquid within the reaction zone above about 4.5, and preferably within the range of 5–7, to prevent the formation therein of acids such as gluconic acid which can leach active metals such as nickel from the catalyst. Loss of such metals causes a permanent decline in catalyst activity and should be avoided. It has been unexpectedly found that high catalyst activity can be maintained and long useful catalyst life achieved by limiting the percent incremental conversion achieved in each reaction zone principally through control of space velocity and also by adding an alkali solution such as sodium hydroxide to the feed stream to each reaction zone to help control the pH of the liquid therein within the desired range. Hydrogen gas is added to the feedstream to each stage sufficient to maintain an excess of hydrogen in the reaction zone.

The first-stage reaction zone preferably uses a back-mixed-type reactor which provides for mixing a portion of the reactor liquid with the feedstream to limit conversion per pass and thereby help control pH of the reactor liquid. The first-stage reactor is more preferably an upflow ebullated-catalyst-bed reactor, which inherently provides not only internal back-mixing of liquids, but also conveniently provides for mixing an alkali solution with the recycled reactor liquid stream to control pH of the reactor liquid within the desired range.

For the fixed-catalyst-bed reactors, the hydrogen flow rate used is quite important and is related to the liquid feed rate and the quantity of catalyst used, as the hydrogen gas flow provides for carrying the feed liquid droplets through the fixed-catalyst-type beds to achieve intimate contact with the catalyst particles. The excess hydrogen forms the continuous phase in the fixed-bed reactor, whereas the liquid flows down over the catalyst particles. Local overheating in the bed is avoided by incipient evaporation of water used as the solvent. It has been found that the ratio of hydrogen gas to liquid feed rate at standard conditions should be within the range of about 500 to 5000 for achieving satisfactory conversion of glucose to sorbitol product. The conditions of hydrogen partial pressure, temperature, and space velocity are selected as previously discussed to achieve at least about 99.8 W % overall conversion of the feed to alditol product.

Reaction zone conditions preferred for achieving a high overall conversion of monosaccharides, such as glucose to sorbitol, are 140°–170° C. (284°–338° F.) temperature, 750–1600 psig hydrogen partial pressure, 1.5–10 $V_f/Hr/V_c$ space velocity, and a volumetric hydrogen/liquid feed ratio of 1000–4000. The space velocity used depends on the desired incremental conversion, and could be as high as 16 for 10–20 W % incremental conversion, and as low as 1.5 for 90–99.8 W % incremental conversion, but is generally in the range of 2–10. The unconsumed hydrogen from the reaction is purified and recirculated through the reaction zones for reuse along with fresh, higher-purity hydrogen as needed.

The catalyst used in the reaction zones is preferably a reduced and stabilized nickel on an inert support such as silica-aluminia, and usually contains 40–70 W % nickel. Useful catalyst sizes are within a broad range of 0.020 to 0.250 inch equivalent diameter particle size, and may be in the form of extrudates, spheres or pellets. For ebullated-bed-type reactors, the catalyst sizes used are usually within the range of 0.020–0.200 inch, and for fixed-bed reactors a pellet- or tablet-form catalyst having 0.050–0.250-inch-diameter range is usually preferred because of its greater ease of handling and operation in the reactors.

This multi-stage process can utilize as feedstock all aldoses, including hexoses (monosaccharides), which are convertible into alditols, including glucose, fructose and mannose, with glucose being the preferred feed for production of sorbitol. The glucose feed can be obtained from corn, potatoes, molasses, celluloses and hemi-celluloses, with the preferred feed being from corn starch when it is desired to produce only minor percentages of mannitol in the sorbitol product.

A preferred process sequence consists of three catalytic reactors connected in series, with the first reactor being a back-mixed-type for providing convenient backmixing of reactor liquid to help control pH of the liquid within a desired range of 4.5–7, and provides glucose conversion of about 60–80 W % to sorbitol. The second and third reactors in series are fixed-bed-type catalytic reactors, which each convert about 10–20 W % of remaining glucose feed to sorbitol while maintaining the liquid pH above 4.5. The pH of the feed solution to each reactor, including the recycled reactor liquid stream for the ehullated-bed reactor, is adjusted back to the range of 7–8.5 by adding an alkali solution, such as calcium hydroxide or sodium hydroxide. Metal impurities in the product are removed in one or more deionization steps. Also, the converted liquid product is usually passed through a carbon adsorbent step to remove minor organic impurities and improve product clarity, color and odor.

It is an important advantage of the present invention that by using a back-mixed-type reactor for the first reacton zone, the pH of the liquid therein can be conveniently maintained in a desired range of 4.5–7 to prevent acid leaching of catalyst by adding an alkali solution material to the reactor recycle liquid. Another advantage for the back-mixed-type, first-stage reactor is that the reaction temperature can be controlledd more closely than for a fixed-bed-type reactor, which is important for the initial conversion to avoid the formation of colored material in the reactor. A third advantage is that the space velocities can be maintained about about 2, which reduces mass transfer limitations of the reaction rates.

DESCRIPTION OF PREFERRED EMBODIMENTS

As shown in FIG. 1, a 20–50 W % glucose solution in water is provided at 10 and its pH is adjusted to a range of 7–8.6 by addition of an alkali solution 11a such as sodium hydroxide at mixing step 11. The resulting mixture is pressurized at 12, hydrogen is added at 13, and the stream is preheated at 14 to at least about 100° C. and usually to 100°–120° C. The preheated stream 15 is then fed into the bottom of reactor 16 containing an ebullated bed of catalyst 16a. Reaction conditions are maintained within the broad range of 130°–180° C. (266°–356° F.) temperature, 500–2000 psig hydrogen partial pressure, and space velocity for 40% glucose solution of at least about 1.5 $V_f/Hr/V_c$ and usually not exceeding about 10 $V_f/Hr/V_c$. The reactor liquid is recycled through downcomer 17 and recirculation pump 26 to maintain the catalyst bed 16a in an expanded or ebullated condition. An alkali solution is added at 17a as needed to control the pH of the reactor liquid to within the range of about 5–8.5. The liquid recycle rate through pump 17 can be varied between zero and about 10 times the feed rate at 10, depending upon the heat generated in the catalyst bed 16a and percent glucose conversion desired therein. The catalyst used contains 40–70 W % nickel deposited on an inert support such as silica-alumina, and has particle size within the range of about 0.020 to 0.200 inch equivalent diameter.

The reactor effluent stream at 18, which contains about 6–10 W % glucose and 24–40 W % sorbitol, is mixed with sufficient alkali solution at 19 to restore the stream pH to a range of 7–8.5. The resulting solution at 20, along with hydrogen added at 21, is introduced into the top of fixed-bed catalytic reactor 24 for further conversion of remaining glucose to sorbitol. If needed, further preheating of stream 20 can be accomplished in heater 22. The reaction conditions used in reactor 24 are substantially the same as for ebullated-bed reactor 16; however, the space velocity is usually increased because of the smaller percent conversion of glucose to sorbitol desired therein. The catalyst used comprises 40–70 W % nickel on an inert support such as silica-alumina, with particle size within the range of about 0.030–0.30 inch equivalent diameter.

The reacted stream 25 is withdrawn and mixed with sufficient alkali material at 27 to restore the stream pH value to 7–8.5. The resulting solution at 30 is introduced along with additional hydrogen at 31 into third fixed-bed, catalytic reactor 34. If desired, further heating of stream 30 can be accomplished in preheater 32. The reactor 34 contains catalyst comprising 40–70 W % nickel on an inert support, and achieves at least about 99.8 W % overall conversion of the glucose to sorbitol.

Used catalyst 16a in ebullated-bed reactor 16 can be withdrawn gradually and replaced with fresh or regenerated catalyst, and thus the catalyst does not require regeneration in place. The catalyst in the fixed-bed reactors 24 and 34 can be regenerated as needed by passing hydrogen gas through the bed at conditions of 300°–350° F. temperature and 100–500 psig pressure for a period of at least about 4 hours.

The resulting sorbitol-water solution at 35 is cooled at 36 and passed to phase separator 38, where the fluid is separated into overhead gas stream 39 and bottoms liquid stream 43. Overhead stream 39, containing mainly hydrogen, is passed to hydrogen purification step 40. The resulting purified hydrogen stream 42, having purity of at least about 75% hydrogen, is recycled through compressor 42 to provide streams 13, 21 and 31 for reuse in the catalytic reaction stages. High-purity makeup hydrogen can be added at 41a as needed.

Liquid stream 43, usually at 750–1600 psig reactor pressure, is pressure-reduced at valve 43a to 25–100 psig and passed to column 44 containing activated carbon adsorbent to remove trace impurities and any objectionable odors from the liquid and to improve its clarity. The treated solution 45 is next passed to cation ion-exchange column 46 containg a suitable resin material, such as Amberlite IRC-120, obtainable from Rohm and Haas Co. for removal of the alkali metal ions added at the feedstream neutralizing steps 11, 19, and 27 located upstream of each catalytic reactor. Also, anion ion-exchange column 48 containing a suitable resin material, such as Amberlite IRC-402, is provided for more complete removal of the acid groups and anion species from stream 47. These ion-exchange columns also provide for removal of any metals which may have been leached from the catalyst in reactors 16, 24 and 34 due to formation of gluconic acid therein.

The effluent stream at 49, usually at near atmospheric pressure, is pressure-reduced at valve 51 and passed to evaporator 50 for removal of excess water and to provide a more concentrated sorbitol solution, with the water vapor being removed at 52. The evaporator pressure is usually maintained within the range of 50-150 mm mercury, with evaporator temperature being maintained in the range of about 20°-45° C. by heating, such as by fluid passage 53 carrying a hot fluid such as steam. The resulting sorbitol-water product solution, which meets USP specification, is withdrawn at 54.

Figure 2:
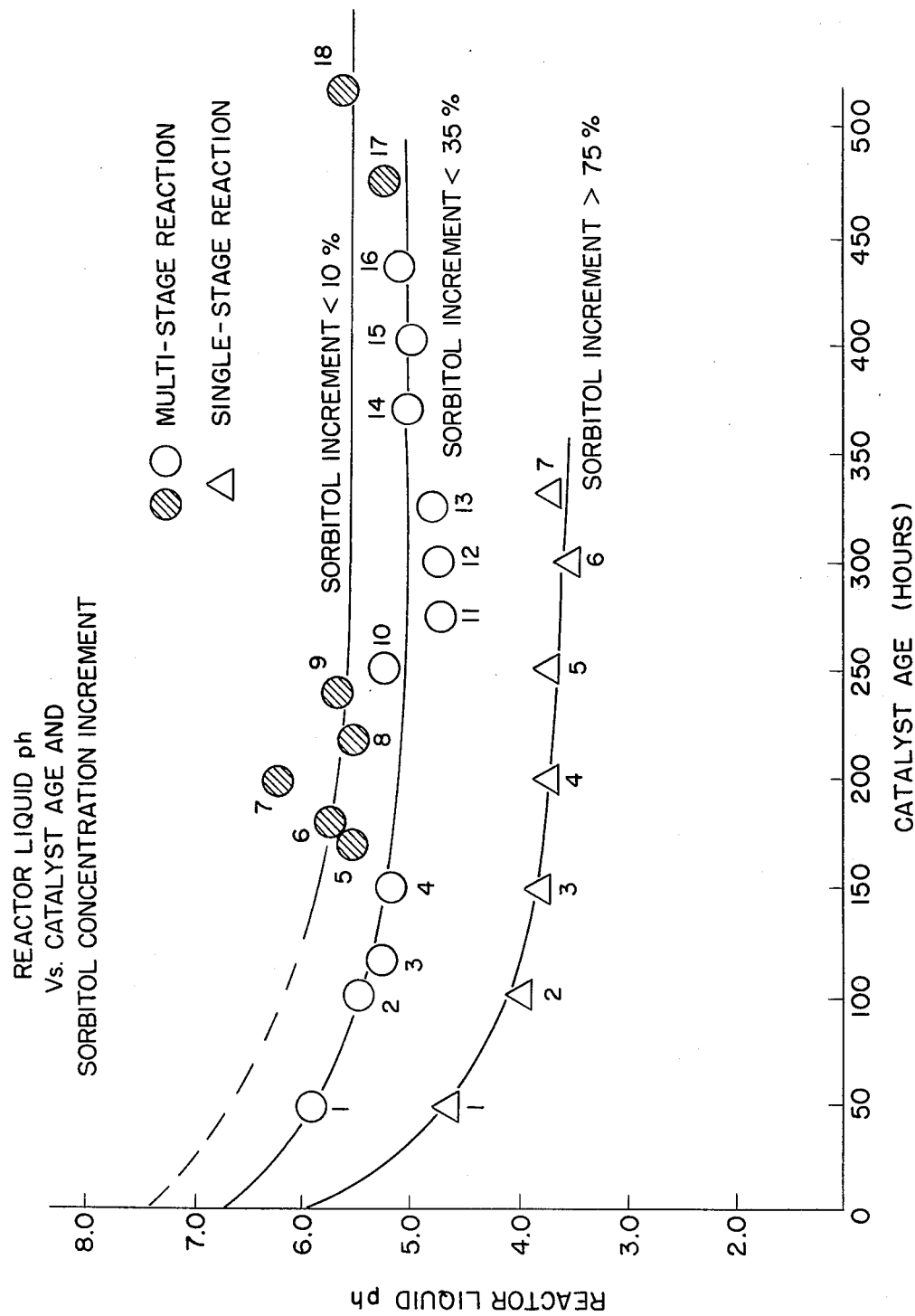
FIG. 2 is a graph showing the relationship between pH of the reactor liquid effluent vs. catalyst age for various percent conversion increments of the glucose feedstream to sorbitol.

It was found that an important relationship exists between the percent conversion of glucose to sorbitol achieved in each reactor, the resulting pH of the reactor effluent stream, and useful catalyst life. This relationship is generally shown in FIG. 2, which shows that for single-stage hydrogenation reaction achieving at least about 75 W % conversion increment, the pH of the reactor liquid declines quickly with increasing catalyst age to about 3.5, evidently due to formation of some gluconic acid in the reactor. But for multi-stage reactions with glucose conversion increment per stage not exceeding about 35 W %, the pH of reactor liquid is maintained above about 4.8 and high catalyst activity can be extended beyond about 500 hours. However, if the percentage glucose conversion increment per reaction stage is further limited to not exceeding about 10 W %, the reactor liquid pH is maintained above about 5.4 and its rate of decline is further reduced and the useful catalyst life is further extended. Thus, it is advantageous to utilize multi-stage reactors connected in series to maintain the reaction liquid pH above about 4.5 to reduce any undesired rate of production of gluconic acid in each reactor and thus maintain very long catalyst life, thereby substantially reducing catalyst cost.

Figure 3:
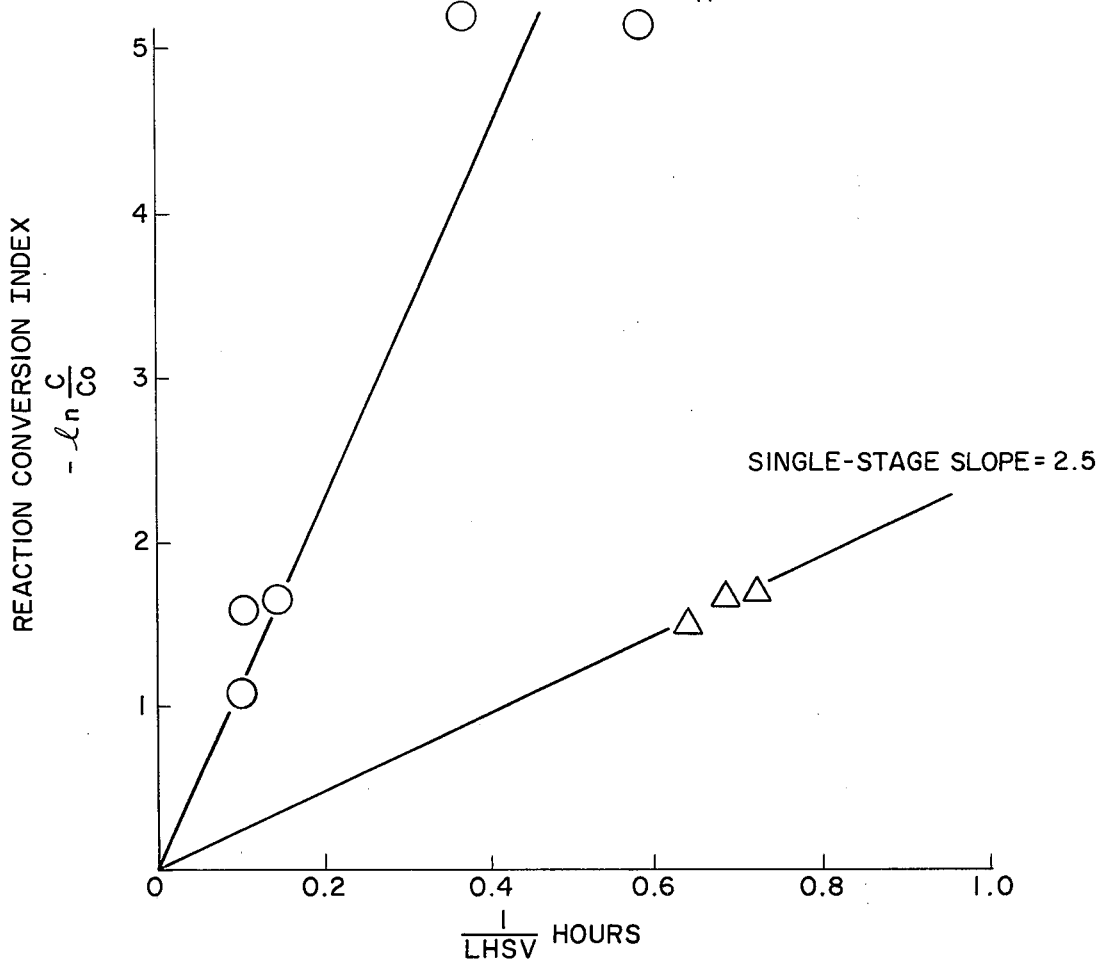
FIG. 3 is a graph showing the general relationship between logarithm of glucose concentration ratio and inverse space velocity for single stage and multi-stage operations.

In this process for catalytic hydrogenation of aldoses, it was also found that controlling reactor liquid pH in the desired range also maintains high catalyst activity. In operations without maintaining reactor liquid pH above about 4.5, such as for the single-stage reaction data in FIG. 2, it is noted that pH dropped to 3.5 and catalyst activity declined to only about 20% of its normal value. However, when reactor liquid pH was maintained above about 4.5, as for multi-stage data shown in FIG. 2, the catalyst activity was maintained at substantially its normal rate after 500 hours catalyst age. This improvement in catalyst activity vs. catalyst age is generally shown in FIG. 3, which shows reaction conversion index as defined by the negative natural logarithm of glucose concentration ratio between reaction zone feed and product plotted vs. inverse space velocity in the reaction zone. It is seen that for single-stage reaction, the catalyst activity represented by slope dropped to 2.5 after 250 hours, but for multi-stage reaction the catalyst activity was maintained at slope of 11.2 even after 500 hours catalyst age.

Figure 4:
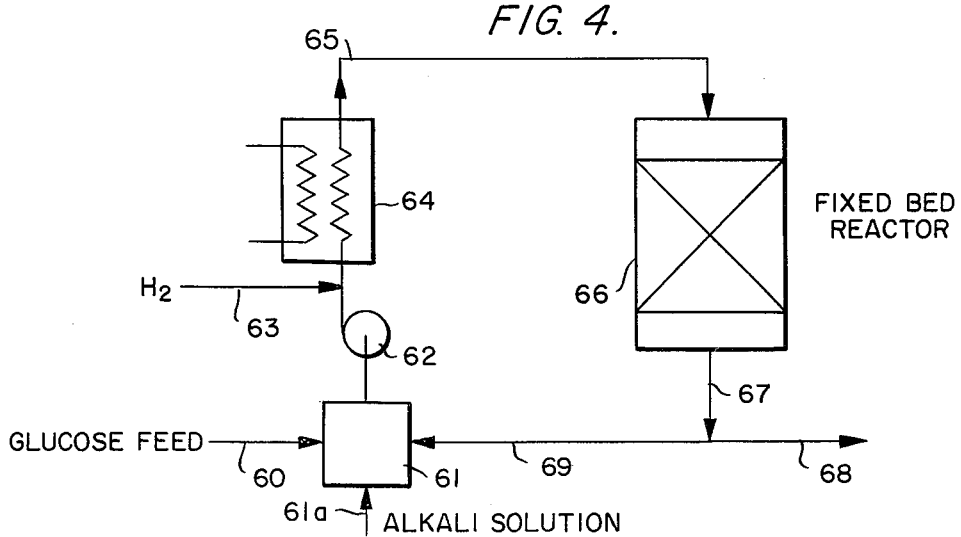
FIG. 4 is a flow diagram of a fixed-bed, back-mixed-type catalytic reactor suitable for the first reaction stage in the process.

In another useful embodiment of this invention, a back-mixed fixed-bed-type catalytic reactor is advantageously used for the first-stage reaction. As shown in FIG. 4, a feedstream at 60 containing 30-50 W % glucose in water solution is mixed in mixing tank 61 with an alkali solution at 61a sufficient to adjust its pH to within the range of 7-10. The resulting liquid mixture is pressurized at 62, hydrogen gas is added at 63, and the stream is preheated at 64 to 100°-120° C. temperature. The preheated stream 66 is then introduced into downflow fixed-bed catalytic reactor 66 containing a high-nickel supported particulate catalyst, and wherein reaction conditions are maintained substantially the same as for ebullated-bed reactor 16 of FIG. 1.

The major portion 69 of reactor effluent stream 67 is recycled to mixing tank 61 to help control pH of the reactor effluent liquid above about 4.8, and usually to within the range of 5-9. The remaining stream 68 is passed on to another catalytic reaction stage for further conversion to sorbitol, similarly as for FIG. 1. The flow ratio of recycled stream 69 to feedstream 60 should be within the range of 2-10.

The invention is further illustrated by reference to the following examples, which should not be construed as limiting the scope of the invention.

EXAMPLE 1

Operation of a back-mixed-type reactor was simulated in operations using a fixed-catalyst-bed reactor. A feedstream, initially containing 40 W % glucose derived from potato starch in water solution, had its pH adjusted to 7 to 8.5 by adding sodium hydroxide solution. The mixture was introduced along with excess hydrogen gas downwardly into the reactor, which was 1 inch inside diameter and 17 inches long. The lower end of the reactor contained about 60 cc catalyst particles, comprising high nickel on silica-alumina support in the form of 0.060-inch diameter extrudates. The reactor upper end contained inert alumina tablets, which served as a preheating and flow distribution section. The reactor was heated with an electrically-heated sand bath to maintain uniform temperatures within the catalyst bed. Hydrogen partial pressure was maintained at 1525 psig. The effluent product stream from the fixed-bed reactor was mixed with sodium hydroxide solution sufficient to restore the stream pH to 7-8.5, and the mixture was added to fresh feed and then recycled through the same reactor an additional number of times. Operating conditions and results of these operations with reactor backmixing are provided in Table 1 below:

TABLE 1

| FIXED BED CATALYTIC REACTOR OPERATIONS USING LIQUID RECYCLE | | | |
|---|---|---|---|
| | First Pass | Second Pass | Third Pass |
| Fresh Feed Used, % | 100 | 30 | 30 |
| Reactor Avg. Temp., °F. | 305 | 305 | 305 |
| Liquid Hourly Space Velocity, cc/Hr/cc | 8.8 | 3.6 | 2.1 |
| Reactor Effluent pH Value | 4.5 | 5.0 | 5.0 |
| Glucose in Feed, W % (Based on Solids) | 100 | 44.6 | 24.6 |
| Sorbitol in Product, W % (Based on Solids) | 72 | 98 | 99.9 |
| Glucose Conversion, W % | 72 | 95.5 | 99.6 |

The results show that for the first pass through the reactor catalytic bed, the glucose conversion was 72 W %. Upon passing a mixture of the reactor effluent containing increased sorbitol and fresh feed containing 40 W % glucose through the catalyst bed a second time at lower space velocity, the conversion was about 85.5 W %, and overall conversion was about 98 W %. Upon passing effluent from the second pass mixed with feed through the reactor a third time, the conversion was 99.6 W %, and overall conversion of glucose 99.9 W %. Thus, these data show that use of a back-mixed reactor, wherein some of the reaction effluent product is mixed with feed and recycled through the reactor again, is practical and beneficial for maintaining reactor liquid pH above about 4.5 and thus preventing acid leaching of the catalyst, and thereby achieving high conversion and extended catalyst life.

EXAMPLE 2

A feedstream containing 40 W % glucose in water solution was introduced with hydrogen gas downwardly into the fixed-catalyst-bed reactor used in Example 1 to determine results of typical second-stage, fixed-bed reactor operations. The lower end of the reactor contained 60 cc of catalyst comprising high nickel on silica-alumina support, in the form of 0.060-inch-diameter extrudates. The reactor upper end contained inert alumina tablets which provided for preheating and flow distribution. Operations were conducted with excess hydrogen at reaction conditions shown in Table 2 below, which also shows the results achieved.

TABLE 2

| FIXED-BED CATALYTIC REACTOR OPERATIONS | | | |
|---|---|---|---|
| Catalyst Age, Hrs | 50 | 100 | 150 |
| Average Reactor Temperature, °C. | 150 | 150 | 150 |
| Hydrogen Partial Pressure, psig | 1525 | 1525 | 1525 |
| Liquid Hourly Space Velocity, $V_f/Hr/V_c$ | 1.33 | 1.53 | 1.46 |
| Reactor Effluent pH Value | 5.0 | 5.0 | 5.0 |
| Glucose Conversion Increment, W % | 39.4 | 39.0 | 39.12 |
| Overall Glucose Conversion, W % | 98.6 | 97.5 | 99.8 |

Results shown in Table 2 indicate that by addition of an alkali solution to help maintain pH of the reactor effluent liquid above about 5.0, the catalyst activity was maintained relatively undiminished for at least about 150 hours.

EXAMPLE 3

A feedstream containing 4 W % glucose monohydrate, 36 W % sorbitol, and 60 W % water was introduced with excess hydrogen gas into the fixed-catalyst-bed reactor used for Example 1 to simulate typical third-stage, fixed-bed reactor operations. The catalyst used was 0.060-inch-diameter extrudates comprising high nickel on silica-alumina substrate. Operations were conducted at reaction conditions typical for a third-stage reactor; the conditions and results are shown in Table 3.

TABLE 3

| FIXED-BED CATALYTIC REACTOR OPERATIONS | | |
|---|---|---|
| Catalyst Age, Hrs. | 10–50 | 90–120 |
| Average Reactor Temperature, °C. | 150 | 150 |
| Hydrogen Partial Pressure, psig | 1525 | 1525 |
| Liquid Hourly Space Velocity, $V_f/Hr/V_c$ | 1.6 | 1.6 |
| Reactor Effluent pH Value | 5.5 | 5.5 |
| Glucose Conversion, W % | 99.78 | 99.73 |

The above typical results show that the overall glucose conversions exceeding 99.95 W % were achieved, and that the catalyst activity was maintained substantially undiminished for up to 120 hours.

EXAMPLE 4

Extended fixed-bed reactor operations were conducted with 40 W % glucose feed at conditions of average temperature of 150° C. and 1100 psig hydrogen partial pressure. The catalyst used contained high concentration of nickel, and had particle size of 8–12 mesh (0.094–0.066 inch). After 240 hours operation, the percent conversion declined from 99.7 to 90%, evidently due to a decline in catalyst activity. The feed was interrupted, and the catalyst was regenerated by passing hydrogen gas through the catalyst bed at about 150° C. and 500 psig pressure for 4 hours. Introduction of glucose feed was then resumed, and the glucose conversion increased to 99.7 W %. It was thus determined that used catalyst can be regenerated by treating it with hot hydrogen gas at conditions of at least about 150° C. and 1 atm. hydrogen partial pressure for a period of at least about 4 hours.

EXAMPLE 5

A feedstream containing 40 W % glucose in water solution and having pH of 8.2 is introduced with hydrogen gas into a back-mixed-type reactor containing an ebullated bed of catalyst particles. The catalyst comprises high nickel on silica-alumina support, and has particle size of 0.05 inch. Reaction conditions are maintained at about 150° C. (302° F.) temperature, 1525 psig hydrogen partial pressure, and 8.1 $V_f/hr/V_c$ liquid hourly space velocity. The catalyst bed expansion is maintained at 20% above its settled height by recycling reactor liquid from a point above the catalyst bed to a flow distributor located below the bed, thus providing for back-mixing of reactor liquid with the fresh feed. The pH of the reactor liquid is maintained within the range of 5.5–7 by mixing it with sufficient sodium hydroxide solution. The conversion of glucose achieved is 80% with a recycle ratio of 10. A stream of partially converted glucose is withdrawn overhead from the reactor and passed to a second catalytic reactor for further conversion of the remaining glucose to sorbitol solution.

Although this invention has been described in terms of the accompanying drawing and preferred embodiment, it will be appreciated by those skilled in the art that many modifications and adaptations of the basic process are possible within the spirit and scope of the invention, which is defined solely by the following claims.

We claim:

1. A multi-stage process for producing high-purity alditol solution by catalytic conversion of monosaccharides, comprising the steps of:
   (a) preheating a feed of at least 10 W % monosaccharides solution in water and hydrogen gas to at least about 100° C., said feed having a pH of 7 to 13 and passing the heated feedstream mixture through multiple catalytic reaction zone connected in series, wherein each zone contains a particulate catalyst comprising high-activity nickel on an inert support;
   (b) mixing an alkali solution with the feed stream to each reaction zone to maintain pH of the effluents of said reaction zones above about 4.5;
   (c) maintaining the reaction zones at conditions within the range of 130°–180° C. temperature, 500–2000 psig hydrogen partial pressure, and 0.5–16 $V_v/hr/V_c$ space velocity, for achieving at least about 98 W % overall conversion of the monosaccharides feed to alditol; and
   (d) withdrawing product containing substantially alditol in water solution.

2. The process of claim 1, wherein the catalyst in each reaction zone contains 40-70 W % stabilized nickel deposited on silica-alumina support, and said catalyst has 0.020 to 0.250-inch diameter particle size and 140-180 M$^2$/gm surface area.

3. The process of claim 1, wherein the pH of the feedstream upstream of each reaction zone is controlled within range of about 8 to 12 by mixing an alkali solution with said feedstream, and wherein the first reaction zone provides for back-mixing a portion of the reaction zone effluent with the feed stream, and the operating parameters are controlled to maintain pH of the liquid in each reaction zone at least above about 4.5.

4. The process of claim 1, wherein the first reaction zone uses an upflow, ebullated-catalyst-bed type reactor which provides for internal back-mixing of reaction zone liquid with the feedstream effluent to maintain said effluent at a pH of 4.5 to 7.0, the last reaction zone is a fixed bed, catalyst-type reactor, and the conditions in each reaction zone are maintained within the range of 140°-170° C., 750-1600 psig hydrogen partial pressure, and 1.0-10 $V_f$/Hr/V space velocity.

5. The process of claim 4, wherein a portion of the reactor liquid in said ebullated-catalyst-bed reaction zone is withdrawn, mixed with an alkali solution, and then recycled to the reactor to help control pH of the liquid therein to within the range of 4.5 to 7.

6. The process of claim 1, wherein the feed to the first reaction zone is 10-60 W % glucose solution in water, and the overall glucose conversion is 98.5-99.9 W % to sorbitol in water solution.

7. The process of claim 1, wherein three reaction zones are used and the ratio of hydrogen gas to liquid feed at standard conditions to each reaction zone is between about 500 and 4000.

8. The process of claim 1, wherein the catalyst is regenerated after conversion declines at least about 5 W % by interrupting the feed and continuing hydrogen flow for at least about 4 hours.

9. The process of claim 1, wherein metal ions are removed from the alditol liquid from step (d) to provide deionized alditol product.

10. The process of claim 1, wherein an activated carbon treatment step is used after the last catalytic reaction step to provide clear alditol product solution.

11. The process of claim 6, wherein the feedstream is potato-derived glucose.

12. The process of claim 6, wherein the feedstream is glucose monohydrate.

13. A process for producing sorbitol by catalytic conversion of glucose, comprising the steps of:
(a) preheating a feed stream containing about 10-60 W % glucose solution in water and added hydrogen gas to about 100°-220° C., said feedstream having pH of 7 to 13 and passing the heated feedstream mixture through three catalytic reaction zones connected in series, each zone containing a high-activity nickel catalyst comprising 40-70 W % nickel deposited on silica-alumina support and having particle size within range of 0.030-0.30 inch equivalent diameter;
(b) mixing an alkali solution with the feedstream to each reaction zone to maintain the pH of the effluent of each reaction zone above about 4.5;
(c) maintaining each reaction zone at conditions within the range of 140°-170° F. temperature, 750-1600 psig hydrogen partial pressure, and 1.5-10 $V_f$/Hr/$V_c$ space velocity, and at hydrogen gas/liquid feed rate of 500-4000 at standard conditions for achieving at least about 99 W % overall conversion of the glucose to sorbitol; and
(d) withdrawing product containing substantially sorbitol in water solution.

14. A process for making alditols by catalytic conversion of aldoses, comprising the steps of:
(a) providing a feedstream containing at least about 10 W % aldose solution in water and having a pH of 7 to 13;
(b) adding hydrogen gas and preheating the feed mixture to at least about 100° C., and passing the heated feedstream mixture through at least two catalytic reaction zones connected in series, each zone containing catalyst comprising 40-70 W % nickel deposited on silica-alumina support;
(c) mixing the feedstream to each reaction zone with an alkali solution to help maintain pH of the effluent from said zones within the range of 4.5 to 7;
(d) maintaining the reaction zones at conditions within the range of 130°-180° C. temperature, 500-2000 psig hydrogen partial pressure, and space velocity within the range of 1.0-15 $V_f$/Hr/$V_c$ to maintain pH of reaction zone effluent stream within the range of 4.5 to 7 for achieving at least about 98 W % overall conversion of the feed to alditols; and
(e) withdrawing product containing substantially alditol in water solution.

15. A process according to claim 14, wherein the first reaction zone provides for back-mixing of a portion of reaction zone liquid with the feedstream and the specific conversion achieved in the first zone is within the range of 40-80 W % of feed material, and the specific conversion achieved in subsequent reaction zones is within the range of 5-20 W %.

16. A process according to claim 14, wherein the feedstream is 20-50 W % mannose solution and the product is substantially mannitol.

17. A process according to claim 14, wherein the feedstream is 20-50 W % xylose solution and the product is substantially xylitol.

18. A process for making alditol by catalytic conversion of aldoses, comprising the steps of:
(a) providing a feedstream containing at least about 10 W % aldose solution in water and having a pH of 7 to 13;
(b) adding hydrogen gas and preheating the feed mixture to at least about 100° C., and passing the heated feedstream mixture through a first-stage catalytic reaction zone containing catalyst comprising 40-70 W % nickel deposited on an inert support, and recycling a portion of reaction zone effluent with the feedstream to control conversion per pass and help maintain reactor effluent liquid pH above at least about 4.5;
(c) mixing said portion of reactor effluent liquid before recycling to said zone with an alkali solution sufficient to maintain pH of the effluent liquid from said zone at least above about 4.5;
(d) passing the mixture from (c) and hydrogen and alkali solution to a second-stage fixed-bed-type catalyst reaction zone containing a particulate catalyst comprising 40-70 W % nickel on an inert support, the amount of alkali solution added to said zone should be sufficient to maintain pH of the effluent liquid of said zone at above about 4.5;

(c) maintaining both reaction zones at conditions within the range of 130°–180° C. temperature, 500–2000 psig hydrogen partial pressure, and 0.5–16 $V_f/Hr/V_c$ space velocity, for achieving at least about 98 W % overall conversion of the feed to alditols; and (f) withdrawing from said second reaction zone a product containing substantially alditol in water solution.

* * * * *